United States Patent
Okamoto

(10) Patent No.: US 12,146,850 B2
(45) Date of Patent: Nov. 19, 2024

(54) DETECTION APPARATUS AND DATA COLLECTION METHOD

(71) Applicant: NATIONAL INSTITUTE FOR MATERIALS SCIENCE, Ibaraki (JP)

(72) Inventor: Akihiro Okamoto, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 536 days.

(21) Appl. No.: 17/600,313

(22) PCT Filed: May 12, 2020

(86) PCT No.: PCT/JP2020/019026
§ 371 (c)(1),
(2) Date: Sep. 30, 2021

(87) PCT Pub. No.: WO2020/235403
PCT Pub. Date: Nov. 26, 2020

(65) Prior Publication Data
US 2022/0214302 A1     Jul. 7, 2022

(30) Foreign Application Priority Data

May 20, 2019   (JP) ................. 2019-094196

(51) Int. Cl.
*G01N 27/327*    (2006.01)
*A61C 19/04*    (2006.01)

(52) U.S. Cl.
CPC ........ *G01N 27/3277* (2013.01); *A61C 19/04* (2013.01)

(58) Field of Classification Search
CPC ..... G01N 27/327–3277; G01N 33/442; G01N 33/388; A61C 19/04; A61B 5/1468–14865
See application file for complete search history.

(56) References Cited

U.S. PATENT DOCUMENTS

| | | | |
|---|---|---|---|
| 5,254,461 A | 10/1993 | Rohrback et al. | |
| 5,978,692 A | * 11/1999 | Vukan ................ | A61B 5/05 600/556 |

(Continued)

FOREIGN PATENT DOCUMENTS

| | | |
|---|---|---|
| JP | 3-9715 | 1/1991 |
| JP | 05-500311 | 1/1993 |

(Continued)

OTHER PUBLICATIONS

EPO machine-generated English language translation of JP 2006-067997 A, downloaded May 4, 2024, patented Mar. 6, 2006 (Year: 2006).*

(Continued)

*Primary Examiner* — Alexander S Noguerola
(74) *Attorney, Agent, or Firm* — Wenderoth, Lind & Ponack, L.L.P.

(57) ABSTRACT

A detection apparatus includes: an electrode formation unit that is brought into contact with an object to form an electrode; a detection unit that constitutes an electrode pair with the electrode; a measurement unit that measures a current flowing between the electrode and the detection unit; and a determination unit that determines presence or absence of an abnormality related to bacteria attached to the object according to the current measured by the measurement unit.

8 Claims, 7 Drawing Sheets

(56) References Cited

U.S. PATENT DOCUMENTS

| | | | |
|---|---|---|---|
| 8,326,413 B1* | 12/2012 | McClain | A61B 5/4547 |
| | | | 433/167 |
| 2008/0197023 A1 | 8/2008 | Miyahara et al. | |
| 2011/0111361 A1 | 5/2011 | Kleinberg et al. | |
| 2012/0077258 A1 | 3/2012 | Förtsch et al. | |
| 2016/0000947 A1* | 1/2016 | Brodbeck | A61L 2/035 |
| | | | 433/32 |
| 2016/0338626 A1* | 11/2016 | Wang | H01M 8/22 |

FOREIGN PATENT DOCUMENTS

| | | |
|---|---|---|
| JP | 2006-067997 | 3/2006 |
| JP | 2012-518161 | 8/2012 |
| JP | 2014-97027 | 5/2014 |
| JP | 2014-097027 | 5/2014 |
| JP | 2016-504949 | 2/2016 |
| JP | 2017-511241 | 4/2017 |
| JP | 2019-140955 | 8/2019 |

OTHER PUBLICATIONS

EPO machine-generated English language translation of JP 2014-4097027 A, downloaded May 4, 2024, patented May 29, 2014 (Year: 2014).*
Extended European Search Report issued Apr. 19, 2023 in corresponding European Patent Application No. 20810158.4.
James V. Halliwell et al., "Voltage clamp techniques", Chapter 2 (Dec. 1999), pp. 17-35, retrieved from the Internet: URL: https://personal.ntdallas.edu/-tres/microelectrode/microelectrodes_ch02.pdf.
International Search Report issued Jul. 21, 2020 in International Application No. PCT/JP2020/019026.

* cited by examiner

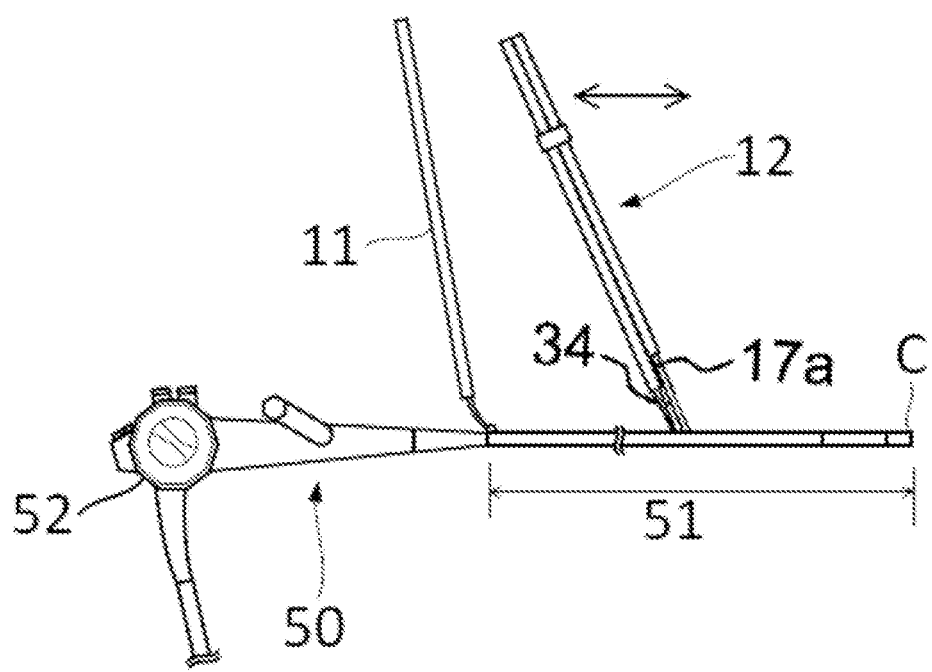

DETECTION APPARATUS AND DATA COLLECTION METHOD

TECHNICAL FIELD

The present invention relates to a detection apparatus and a data collection method.

BACKGROUND ART

There is a demand for detecting abnormalities related to bacteria attached to various objects.

Here, a dental implant treatment is a treatment method for joining an artificial tooth to which the functions and form of a tooth are imparted on a fixture that is an artificial tooth root embedded in the jawbone.

The artificial tooth may be directly coupled to the fixture (one-piece type) or may be fixed to an abutment (abutment portion) fixed to the fixture (two-piece type).

Since dental implants are stored in the oral cavity and used for a long period of time, it is known that bacteria attached between the dental implant and the gums are activated and/or proliferate depending on an environment in the oral cavity, thereby causing pen-implant mucositis.

As a dental implant for preventing such a disease caused by bacteria, Patent Literature 1 describes "a dental implant (118) or an element thereof comprising a transmucosal portion (122), wherein at least a part of the transmucosal portion (122) includes a biocide (132) and/or a pH adjuster".

CITATION LIST

Patent Literature

Patent Literature 1: JP 2017-511241 A

SUMMARY OF INVENTION

Technical Problem

In order to prevent inflammation caused by bacteria occurring around the dental implant, a method in which a dentist diagnoses a state of a tissue around the implant (for example, examination of a probing depth, observation of bleeding at the time of probing, confirmation of presence or absence of drainage, and the like) is often adopted in a periodic examination by the dentist.

However, according to the above method, although it is possible to detect a state in which inflammation has already occurred, there is a problem that it is not possible to detect a situation before inflammation occurs, specifically, a situation in which the activity of bacteria improves or bacteria starts to proliferate. Note that the problems of abnormalities related to bacteria may occur not only in dental implants but also in various objects.

Therefore, an object of the present invention is to provide an apparatus capable of easily obtaining information for determining presence or absence of an abnormality related to bacteria attached to an object. In addition, another object of the present invention is to provide a data collection method.

Solution to Problem

As a result of intensive studies to achieve the above objects, the present inventor have found that the above objects can be achieved by the following configurations.

[1] A detection apparatus including an electrode formation unit that is brought into contact with an object to form an electrode, a detection unit that constitutes an electrode pair with the electrode; a measurement unit that measures a current flowing between the electrode and the detection unit, and a determination unit that determines presence or absence of an abnormality related to bacteria attached to the object according to the current measured by the measurement unit.

[2] The detection apparatus according to [1], in which the object is a dental implant.

[3] The detection apparatus according to [1] or [2], in which the detection unit further includes an electron source emission unit capable of emitting an electron source.

[4] The detection apparatus according to any one of [1] to [3], further including a reference electrode.

[5] The detection apparatus according to any one of [1] to [4], in which the determination unit includes a comparison unit that compares the current with a predetermined reference, and an abnormality detection unit that detects the abnormality on the basis of a result of the comparison, and the abnormality detection unit prompts to display attention calling information in a case where the abnormality detection unit detects the abnormality.

[6] The apparatus according to [5], in which the attention calling information is information for informing that bacteria may be proliferating.

[7] A data collection method including a step of forming an electrode by bringing an electrical conductor into contact with an object in contact with an electrolytic solution, a step of forming an electrode pair by bringing an electrode different from the electrode into contact with the electrolytic solution, the electrode pair being arranged apart from each other via the electrolytic solution, and a step of measuring a current flowing between the electrode pair.

Advantageous Effects of Invention

According to the present invention, it is possible to provide an apparatus capable of easily obtaining information for evaluating the activity of bacteria around a dental implant. In addition, the present invention can also provide a data collection method.

BRIEF DESCRIPTION OF DRAWINGS

FIG. 7 is a schematic diagram illustrating a usage aspect of a detection apparatus according to a second embodiment of the present invention.

DESCRIPTION OF EMBODIMENTS

First Embodiment

[Detection Apparatus]

A detection apparatus 10 according to a first embodiment of the present invention will be described with reference to the drawings.

The detection apparatus 10 detects an abnormality related to bacteria attached to a dental implant (exemplifying an object). The abnormality related to bacteria is, for example, activation of bacteria or proliferation of bacteria or the like.

Figure 1:
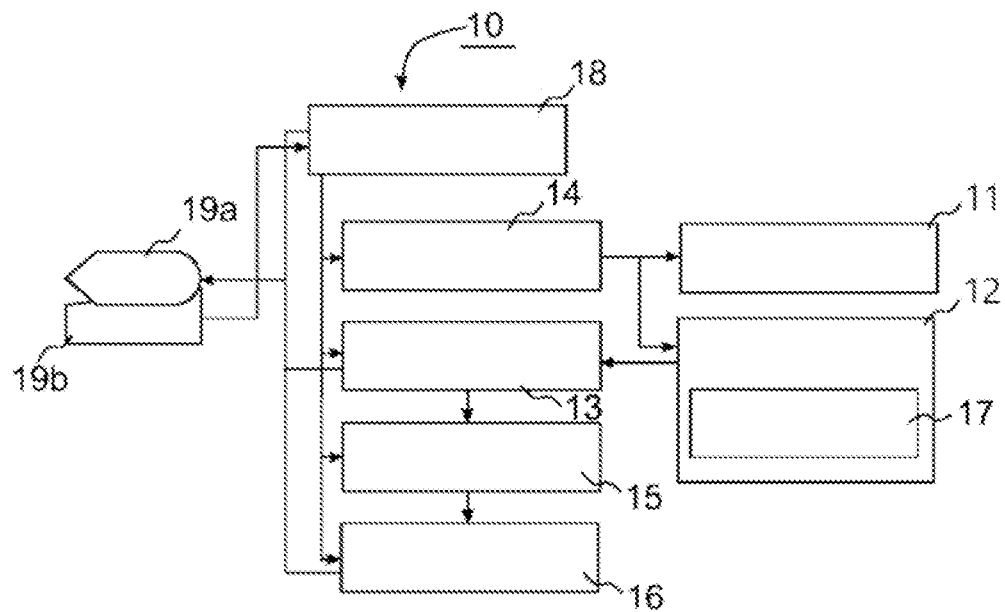
FIG. 1 is a block diagram of a detection apparatus according to a first embodiment of the present invention.
Figure 2:
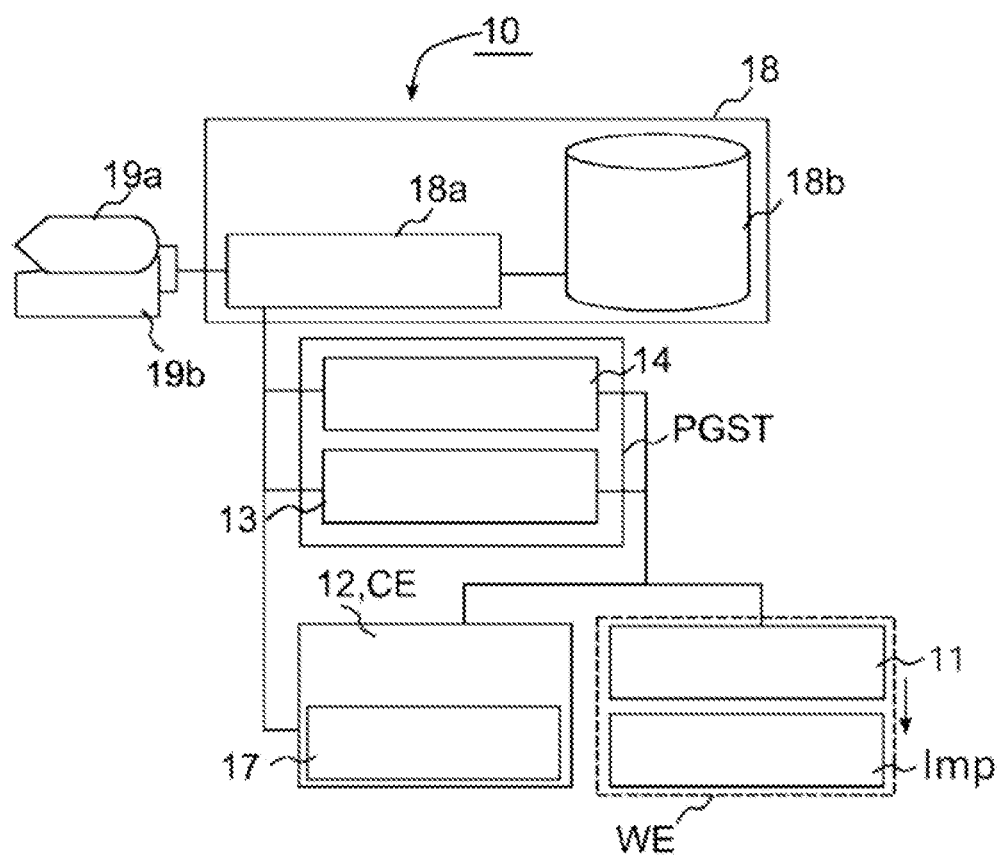
FIG. 2 is a hardware configuration diagram of the detection apparatus according to the first embodiment of the present invention.
Figure 3:
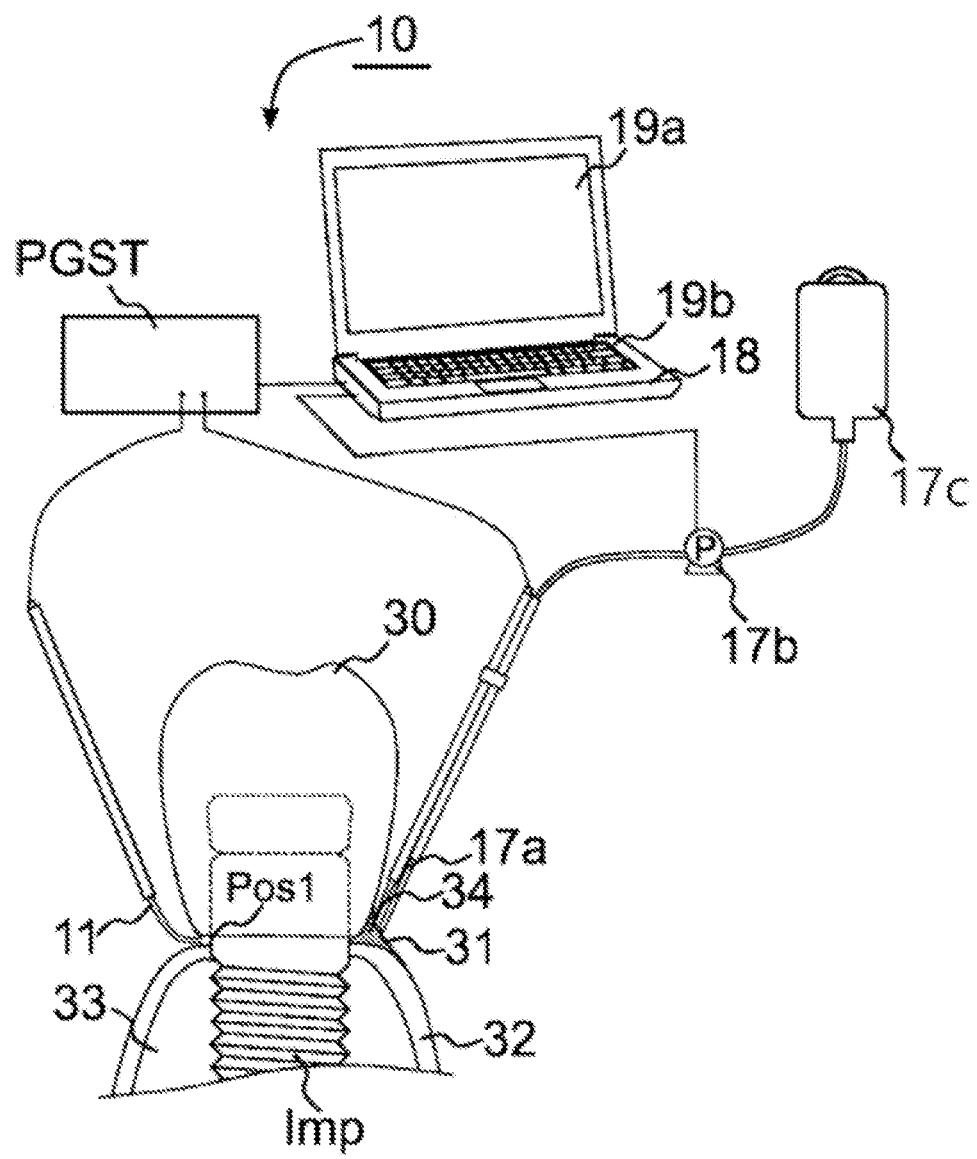
FIG. 3 is a schematic diagram illustrating a usage aspect of the detection apparatus according to the first embodiment of the present invention.

FIG. 1 is a block diagram of the detection apparatus 10, FIG. 2 is a hardware configuration diagram of the detection apparatus 10, and FIG. 3 is a schematic diagram of the detection apparatus 10.

The detection apparatus 10 illustrated in FIG. 1 includes an electrode formation unit 11, a detection unit 12, a measurement unit 13, an adjustment unit 14, a comparison unit 15, an abnormality detection unit 16, an electron source emission unit 17, a control unit 18, and an input/output device including a display device 19a and an input device 19b.

Among those units and devices, the control unit 18 includes a central processing unit 18a and a storage device 18b, and the comparison unit 15 and the abnormality detection unit 16 correspond to a program stored in the storage device 18b and to the central processing unit 18a. In addition, the adjustment unit 14 and the measurement unit 13 are controlled by the control unit 18, and the detection unit 12, the electron source emission unit 17, which is constituted integrally with the detection unit 12, and the electrode formation unit 11 are controlled by the control unit 18 via the adjustment unit 14 and the measurement unit 13.

As illustrated in FIG. 2, in the detection apparatus 10, the electrode formation unit 11 and a dental implant Imp are brought into contact with each other to form one electrode (working electrode WE). That is, the electrode formation unit 11 forms the working electrode WE by coming into contact with the dental implant Imp. In the present specification, the "dental implant" means a one-piece type fixture and abutment and a two-piece type fixture and abutment and usually includes a conductive material such as titanium or a titanium alloy.

The dental implant Imp is usually arranged in the oral cavity, and the periphery thereof is wetted with an electrolytic solution such as saliva.

The detection unit 12 constitutes an electrode (counter electrode CE) paired with the working electrode WE, and the working electrode WE and the counter electrode CE are arranged apart from each other via the electrolytic solution.

The electrode formation unit 11 and the detection unit 12 are electrically connected via the measurement unit 13, and the measurement unit 13 can measure a current flowing between the working electrode WE and the counter electrode CE.

The present inventor has conducted intensive studies to electrochemically detect the activity of bacteria in the oral cavity. As a result, it has been found that bacteria transfer electrons to an extracellular solid (electron conductor), thereby obtaining energy in a state in which the bacteria can exert pathogenicity. Note that becoming a state in which pathogenicity can be exhibited means, for example, becoming a state in which a biofilm is formed as a result of activation or proliferation of bacteria (that is, occurrence of an abnormality related to bacteria) and a state in which the biofilm is acidified. Note that the biofilm is a membrane formed by attachment of bacteria to a surface.

Specifically, regarding *Streptococcus mutans* bacteria cultured under acidic conditions (pH 4) and *Streptococcus mutans* bacteria cultured under neutral conditions, the present inventor observed sections stained specifically for oxidation-reduction reaction with a transmission electron microscope and found that the surface of a cell wall and an inner cell membrane are specifically stained in a case where the *Streptococcus mutans* bacteria are cultured under acidic conditions.

In addition, it has also been confirmed that *Capnocytophaga ochracea* bacteria, which are also known as causative bacteria of periodontal diseases, specifically express electron transfer enzymes in an anaerobic environment.

The above illustrates that biofilm formation, metabolism in the biofilm, and acidification of the biofilm and occurrence of a current (electron transfer to the extracellular solid) have a close relationship each other.

Figure 4:
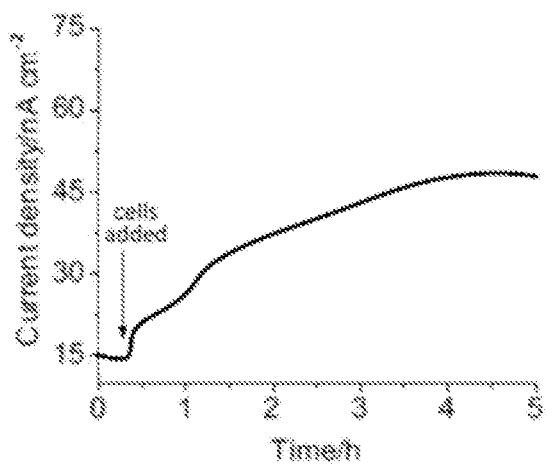
FIG. 4 is a graph illustrating experimental results by the inventor of the present invention.

The present inventor conducted an experiment to examine electron transfer in the intraoral bacteria that are *Streptococcus mutans* (*S. mutans*) under acidic conditions. FIG. 4 is a graph illustrating experimental results (temporal changes in a current) regarding electron transfer in the intraoral bacteria. Note that the current was measured by an anaerobic reactor device including three electrodes (reference electrode, working electrode, and indium tin oxide (ITO) electrode). The current was measured in the presence of the intraoral bacteria in the presence of 10 mM glucose (electron source). Note that intraoral bacteria cultured in an acidic unbuffered solution (pH 4.6±0.2) were used. Specifically, each electrode was arranged in a culture solution of the intraoral bacteria in which 10 mM glucose was present, and a current flowing between the working electrode and the ITO electrode when an electric potential was applied was measured.

As can be grasped from FIG. 4, it has been found that a detected current increases with time. That is, it can be said that electron transfer in the intraoral bacteria become active with the lapse of time. A state in which electron transfer become active is considered to be a state in which a biofilm is formed on the surface of the electrode and the intraoral bacteria are activated and proliferating. Note that, it is considered that a current value correlates with the number of the intraoral bacteria. Utilizing the above findings, the detection apparatus 10 of the present invention employs a configuration in which an abnormality related to bacteria is detected according to a change in a current flowing between electrodes.

Note that in FIG. 4, the temporal changes in the current are detected over several hours, but a time length for detecting temporal changes in the current is any length. For example, in the detection apparatus 10 of the present invention, a temporal change in the current may be detected for a very short time length (for example, for several seconds).

As understood from the above description, in a case where there is an abnormality related to bacteria around the dental implant (for example, in a case where the bacteria are activated and/or proliferating), it is presumed that the bacteria obtain energy by transferring surplus electrons to the dental implant that is an extracellular solid.

In the detection apparatus 10, the dental implant Imp is formed as one electrode and is connected to the counter electrode CE (detection unit 12) via the measurement unit 13. Therefore, the detection of the current value in the detection apparatus 10 means a state in which electron transfer from the bacteria to the dental implant Imp has occurred, that is, a state in which the bacteria can exert pathogenicity (for example, a state in which a biofilm is formed and a state in which the biofilm is acidified). Eventually, it is a state in which an abnormality related to the bacteria attached to the dental implant Imp has occurred. As understood from the above description, it can also be said that the current flowing between the electrode pair reflects an activity situation of the bacteria present around the working electrode WE and the counter electrode CE (for example, a situation of activation of the bacteria or a situation of proliferation of the bacteria).

By scanning over the dental implant Imp with the detection unit 12 and observing a change in the current value during the scan, it is possible to specify a place where the above-described abnormality has occurred (abnormality occurrence position).

Conventionally, it is general that as for inflammation caused by bacteria occurring between a dental implant and the gums, it is confirmed visually that inflammation had occurred and then the inflammation is addressed. In contrast, by using the detection apparatus 10, the abnormality occurrence position can be easily and quickly specified, and the abnormality can also be detected at a stage before visible inflammation occurs.

In addition, the detection apparatus 10 includes the adjustment unit 14. The adjustment unit 14 applies an electric potential between the working electrode WE formed by the electrode formation unit 11 and the counter electrode CE that is the detection unit 12. Since the detection apparatus 10 includes the adjustment unit 14, even in a case where the number of cells of the bacteria is small, a more excellent response speed can be obtained by applying an electric potential between both electrodes. The form of the adjustment unit 14 is not particularly limited, but typically, a potentio/galvanostat (P/G stat, illustrated a symbol "PGST" in FIG. 2) including the measurement unit 13 and the adjustment unit 14 can be used.

Note that the detection apparatus 10 includes the adjustment unit 14, but the detection apparatus 10 according to the first embodiment of the present invention may not include the adjustment unit 14. In a state in which the bacteria exhibit pathogenicity, it is presumed that the bacteria transfer electrons to the dental implant Imp that is an extracellular solid (electrical conductor) to obtain energy. That is, in a case where the bacteria exhibit pathogenicity, it is possible to detect a current without applying an electric potential if a connection to the counter electrode CE and the dental implant Imp is made to form a circuit.

In FIG. 3, the dental implant Imp is embedded in a jawbone 33, and an artificial tooth 30 is fixed to a tip portion. A part of the dental implant Imp is exposed from gums 32. The electrode formation unit 11 is brought in contact with the dental implant Imp at an exposed portion Pos1, and the electrode formation unit 11 and the dental implant Imp constitute the working electrode WE.

Meanwhile, the detection unit 12 includes an electrode 34 and the electron source emission unit 17. The electron source emission unit 17 includes a nozzle 17a for emitting an electron source (typically, an aqueous solution containing an electron source), an electron source storage unit 17c communicating with the nozzle 17a via a pipe, and a pump 17b arranged in the pipe, and the electron source emission unit 17 is configured so that a predetermined amount of the electron source is emitted by operating the pump 17b controlled by the control unit 18.

The electrode 34 is arranged so as to come in contact with an electrolytic solution 31 (typically saliva) present around the dental implant Imp and is arranged with the working electrode WE via the electrolytic solution 31 to function as the counter electrode CE. Each of the electrodes is electrically connected by the potentio/galvano (P/G) stat PGST, and a current flowing between both electrodes can be measured.

The electron source emitted from the electron source emission unit 17 is not particularly limited, and examples thereof include glucose, lactic acid, and the like. The electron source emission unit 17 may emit the electron source itself and may emit a solution containing the electron source. Typically, an aqueous solution containing the electron source can be used, and examples thereof include physiological saline containing the electron source and the like.

Figure 5:
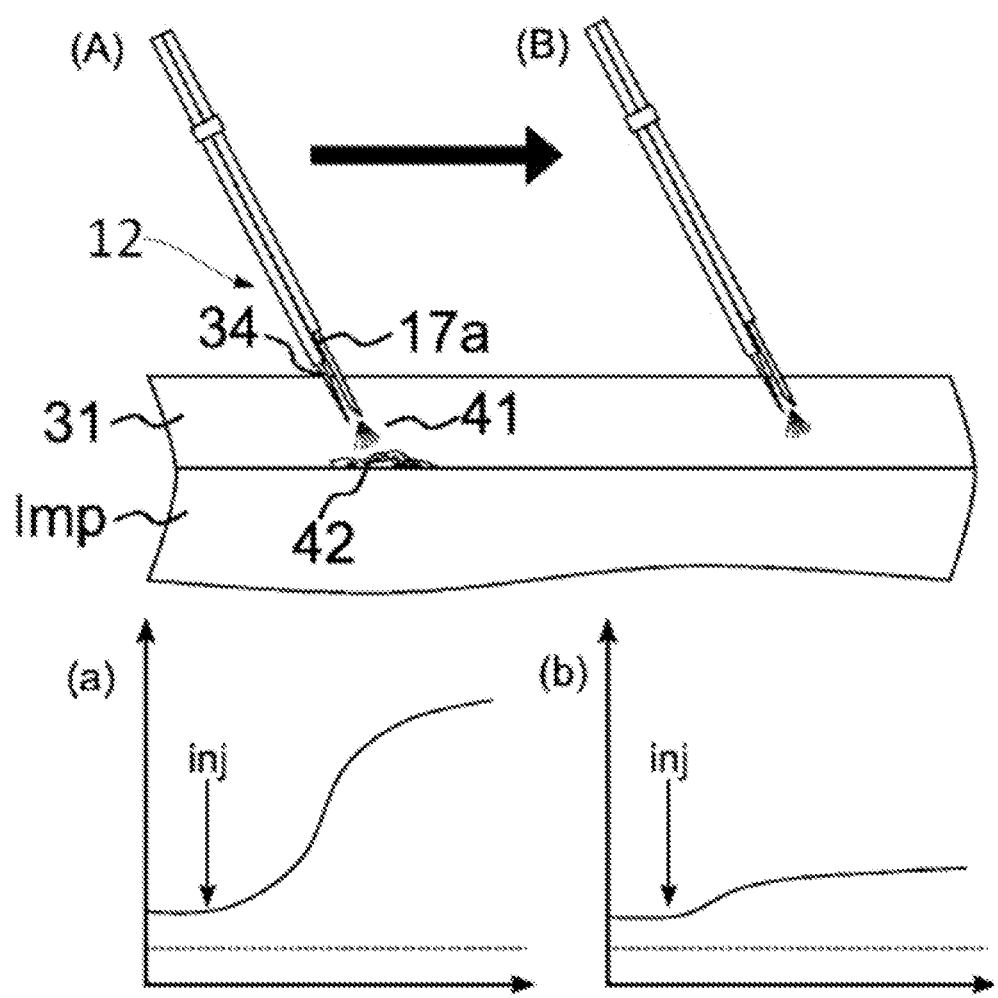
FIG. 5 is a schematic diagram illustrating a method of detecting occurrence of an abnormality by the detection apparatus and specifying an abnormality occurrence position according to the first embodiment of the present invention.

FIG. 5 is a schematic diagram illustrating a method of detecting the occurrence of the abnormality by the detection apparatus 10 and specifying the abnormality occurrence position. In FIG. 5, a fine biofilm 42 is formed on the dental implant Imp, and the bacteria are activated.

FIG. 5(a) schematically illustrates a response detected by the measurement unit 13 with a horizontal axis representing observation time and a vertical axis representing a current. A broken line illustrates a response in a case where there is no abnormality (in a case where there is no electron transfer), and a solid line illustrates a response in a case where there is an abnormality (in a case where there is electron transfer).

The biofilm 42 is formed on the dental implant Imp, and electron transfer from the bacteria to the dental implant Imp occurs. According to the detection apparatus 10, the occurrence of the abnormality can be detected by detecting a current caused by the electron transfer.

In addition, since the detection apparatus 10 includes the detection unit 12 formed by integrating the electrode 34 and the electron source emission unit 17 (nozzle 17a), it is possible to specify the abnormality occurrence position by scanning over the dental implant Imp with the detection unit 12.

A scan is performed from a position illustrated by (A) to a position illustrated by (B) in FIG. 5 with the detection unit 12. At this time, a response measured at the position of (A) is defined as (a), and a response measured at the position of (B) is defined as (b).

First, at the position of (A), an electron source 41 emitted from the nozzle 17a is more likely to reach the bacteria in the biofilm 42, at the position of (A), and thus, as illustrated in (a), the detected current increases after emission inj of the electron source 41.

Meanwhile, at the position of (B), the electron source 41 emitted from the nozzle 17a is less likely to reach the biofilm 42 due to the bacteria in the biofilm and thus the current increases more gradually or does not increase.

That is, by examining a response while scanning with the detection unit 12, it can be specified that the electron source is consumed and the current value increases, that is, the activity of the bacteria increases in a portion where a larger current is obtained as compared with the surroundings.

Since the detection apparatus 10 includes the electron source emission unit 17, the detection apparatus 10 can detect a smaller amount of the bacteria and has a wider dynamic range and/or has a faster response speed.

Note that the detection apparatus 10 includes the electron source emission unit 17, but the detection apparatus 10 according to the first embodiment of the present invention is not limited to the above and may not include the electron source emission unit 17.

In the detection apparatus 10 of FIG. 3, the electron source emission unit 17 includes the nozzle 17a for emitting the electron source (typically, an aqueous solution containing an electron source), the electron source storage unit 17c communicating with the nozzle 17a via a pipe, and the pump 17b arranged in the pipe, and the electron source emission unit 17 is configured so that a predetermined amount of the electron source is emitted by operating the pump 17b controlled by the control unit 18.

Note that in the detection apparatus 10, the detection unit 12 and the electron source emission unit 17 are integrally formed, and the electron source emitted from the electron source emission unit 17 can be more efficiently arranged between the detection unit 12 and the dental implant Imp.

Note that the detection apparatus 10 according to the first embodiment of the present invention is not limited to the above, and the detection unit 12 and the electron source emission unit 17 may be arranged separately.

In addition, in the detection apparatus 10, an amount of the electron source emitted by the electron source emission unit 17 and a timing when the electron source is emitted by the electron source emission unit 17 are controlled by the control unit 18, but the detection apparatus 10 according to the first embodiment of the present invention is not limited to the above, and the operation and stop of the pump 17b may be controlled by an operator.

The measurement unit 13 measures the current between the working electrode WE and the counter electrode CE. When the current is measured, a measurement ID is generated by the measurement unit 13, and data on time from the start of the measurement and a current value obtained at corresponding observation time is generated and stored for each measurement ID in an area secured in the storage device 18b.

The data generated by the measurement unit 13 is passed to the comparison unit 15. The comparison unit 15 compares the data generated by the measurement unit 13 with a predetermined reference (hereinafter referred to as a "reference threshold"). For example, the comparison unit 15 extracts data on the current value at a predetermined observation time and compares the extracted data with the reference threshold. Specifically, the comparison unit 15 compares whether the extracted data exceeds the reference threshold.

A result of the comparison is passed to the abnormality detection unit 16. The abnormality detection unit 16 detects an abnormality related to the bacteria attached to the dental implant Imp on the basis of the result of the comparison by the comparison unit 15. Specifically, in a case where the comparison unit 15 determines that the extracted data exceeds the reference threshold, the abnormality detection unit 16 determines that there is an abnormality related to the bacteria attached to the dental implant Imp. Then, the abnormality detection unit 16 prompts the display device 19a to display the measurement result, and the process ends.

Meanwhile, in a case where the comparison unit 15 determines that the extracted data is less than the reference threshold, the abnormality detection unit 16 determines that there is no abnormality related to the bacteria attached to the dental implant Imp.

As understood from the above description, the comparison unit 15 and the abnormality detection unit 16 function as a "determination unit" for determining the presence or absence of an abnormality related to the bacteria attached to the dental implant Imp according to the current measured by the measurement unit 13. Note that it is not essential for the abnormality detection unit 16 to prompt the display device 19a to display the measurement result.

Note that in FIG. 3, the display device 19a and the input device 19b, and the P/G stat PGST including the measurement unit 13 and the adjustment unit 14 are constituted separately but may be constituted integrally.

In addition, although the detection apparatus 10 includes the display device 19a and the input device 19b, the detection apparatus 10 according to the first embodiment of the present invention may not include the display device 19a and the input device 19b. In that case, a tablet terminal or the like that can wirelessly communicate with the detection apparatus 10 can also be used as a display device and an input device.

In addition, in a case where as a result of the comparison by the comparison unit 15, the extracted data does not satisfy a reference, the abnormality detection unit 16 prompts the display device 19a to display attention calling information. The attention calling information typically means that the activity of the bacteria improves or the bacteria may be proliferating on an implant surface, more specifically, on a measurement target site (position of the detection unit 12). By performing this operation while scanning over the dental implant Imp with the detection unit 12, it is possible to specify the abnormality occurrence position on the dental implant Imp.

Since in the detection apparatus 10, the dental implant Imp serves as one electrode, and the detection unit 12 serves as the other electrode, it is possible to easily obtain information for evaluating the activity of the bacteria in a narrow range around the detection unit 12. Even for the same tooth, it is possible to easily obtain information for evaluating the activity of the bacteria in a narrow range by dividing the tooth into sites on a buccal side (lip side), a palate side (tongue side), and the like.

Note that the detection apparatus 10 may further include a reference electrode. In a case where the detection apparatus 10 includes the reference electrode, an electrode potential can be measured. In a case where the detection apparatus 10 includes the reference electrode, the detection apparatus 10 may be arranged independently from the electrode formation unit 11 and the detection unit 12 or may be arranged integrally with the electrode formation unit 11 and/or the detection unit 12. In particular, it is preferable that the detection unit 12 and the reference electrode are constituted integrally from the viewpoint of easier handling.

[Data Collection Method]

Figure 6:
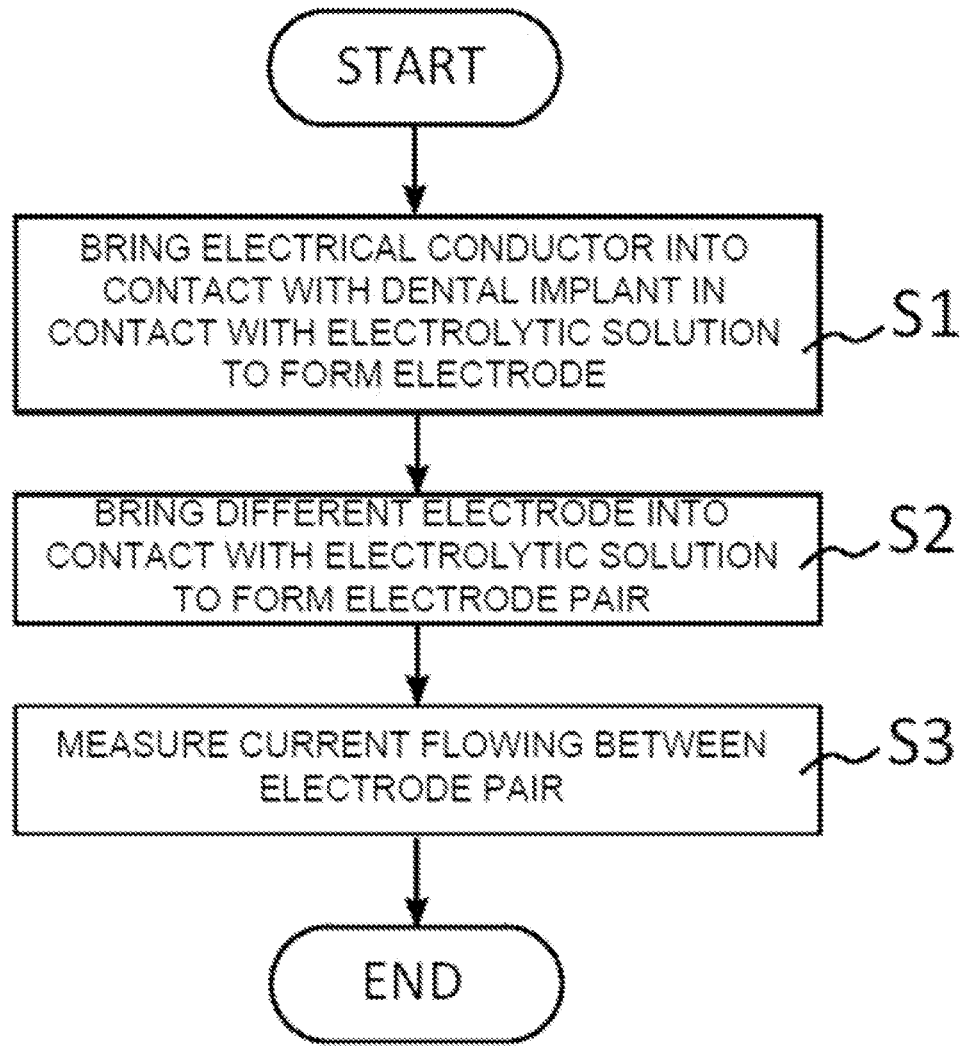
FIG. 6 is a flowchart of a data collection method according to the first embodiment of the present invention.

A data collection method of the present invention is a data collection method including a step of forming an electrode by bringing an electrical conductor into contact with a dental implant in contact with an electrolytic solution, a step of forming an electrode pair by bringing an electrode different from the electrode into contact with the electrolytic solution, the electrode pair being arranged apart from each other via the electrolytic solution, and a step of measuring a current flowing between the electrode pair. FIG. 6 is a flowchart of the data collection method.

First, an electrical conductor is brought into contact with a dental implant in contact with an electrolytic solution to form an electrode (S1). The electrical conductor is not particularly limited, and examples thereof include carbon, gold, platinum, silver, molybdenum, cobalt, nickel, palladium, ruthenium, and the like, and the electrical conductor may be indium tin oxide or the like. In addition, a shape and the like are not particularly limited, but the shape is preferably a probe shape or a wire shape from the viewpoint of easier contact with the dental implant.

Next, an electrode different from the electrode is brought into contact with the electrolytic solution (S2). Here, the electrolytic solution is typically preferably saliva around the dental implant or the like and may be a mixture of an aqueous solution containing an electron source (for example, physiological saline containing glucose) and saliva.

A material of the electrode is not particularly limited, and the materials exemplified above as the electrical conductor can be used. In addition, a shape and the like are not particularly limited, but the shape is preferably a probe shape or a wire shape the viewpoint of easier contact with the dental implant.

An electrode pair is formed as described above, and then a current flowing between the electrode pair is measured (S3). The current reflects the activity of pathogenic microorganisms around the dental implant. Thus, data collected using the above data collection method (current measured at S3) can be used to evaluate the activity of pathogenic microorganisms around the dental implant.

Second Embodiment

A second embodiment of the present invention will be described. Note that elements having actions or functions similar to those of the first embodiment in embodiments exemplified below will be appropriately omitted from detailed description by using reference signs used in the description of the first embodiment.

FIG. 7 is a schematic diagram illustrating a usage aspect of a detection apparatus 10 according to the second embodiment. In FIG. 7, only an electrode formation unit 11 and a detection unit 12 in the detection apparatus 10 are illustrated for convenience. In the first embodiment, an abnormality related to the bacteria attached to the dental implant is detected, but in the second embodiment, an abnormality related to bacteria attached to an endoscope 50 (exemplifying an object) is detected. Note that a configuration of the detection apparatus 10 is similar to that of the first embodiment.

The endoscope 50 is a medical device for observing the inside of the human body (for example, the gastrointestinal tract and the large intestine). Specifically, the endoscope 50 includes an insertion unit 51 and an operation unit 52. The insertion unit 51 is a portion to be inserted into the human body. An imaging element C capable of imaging the inside of the human body is mounted at a distal end of the insertion unit 51. The operation unit 52 is an operator operated by an operator (typically, a doctor).

In the second embodiment, an abnormality related to the bacteria attached to the insertion unit 51 of the endoscope 50 is detected. The electrode formation unit 11 is in contact with the insertion unit 51, and the electrode formation unit 11 and the insertion unit 51 constitutes a working electrode WE. In addition, the detection unit 12 constitutes an electrode (counter electrode CE) paired with the working electrode WE. Then, as in the first embodiment, the working electrode WE and the counter electrode CE are arranged apart from each other via an electrolytic solution. Note that in the second embodiment, for example, physiological saline is used as the electrolytic solution.

In the detection apparatus 10 of the second embodiment, a scan over the insertion unit 51 is performed with the detection unit 12, and a change in a current value during the scan is observed as in the first embodiment. As in the first embodiment, in a state in which the bacteria exhibit pathogenicity, the bacteria transfer electrons to the insertion unit 51 that is an extracellular solid (electrical conductor). Therefore, a current is detected by a measurement unit 13.

As in the first embodiment, the measurement unit 13 measures a current between the working electrode WE and the counter electrode CE. As in the first embodiment, the comparison unit 15 compares data on the current value measured by the measurement unit 13 with a reference threshold. Then, as in the first embodiment, an abnormality detection unit 16 detects an abnormality related to bacteria attached to the insertion unit 51 on the basis of a result of the comparison by the comparison unit 15.

Also in the second embodiment, effects similar to the effects of the first embodiment are achieved. In addition, since the endoscope 50 is inserted into the human body, an abnormality particularly related to bacteria becomes a problem. For example, when the endoscope 50 is inserted into the human body in a state in which the bacteria attached to the insertion unit 51 are activated or proliferate, an infection or the like may occur. According to the detection apparatus 10 of the second embodiment, it is possible to easily and quickly detect the abnormality related to bacteria attached to the endoscope 50.

Note that in FIG. 7, a configuration for detecting an abnormality related to bacteria attached to the surface of the insertion unit 51 has been exemplified, but a portion for detecting an abnormality related to bacteria in the endoscope 50 is not limited to the above example. For example, an abnormality related to bacteria in the operation unit 52 may be detected.

In addition, an object to be detected for an abnormality related to bacteria is not limited to the dental implant and the endoscope. Various articles capable of functioning as electrodes are exemplified as the object. For example, various medical instruments such as surgical instruments (for example, scalpels and forceps) and cannulas are exemplified as the object. Note that in a case where a tubular article such as a cannula is used as the object, it is also possible to detect an abnormality related to bacteria attached to the inside of a tube by inserting the detection unit 12 into the tube. In addition, various devices used in food factories, factories manufacturing precision devices, and the like may be used as the object. As understood from the above description, various objects in which occurrence of bacteria is a problem are targets for detecting an abnormality related to bacteria in the detection apparatus of the present application.

INDUSTRIAL APPLICABILITY

Bacteria attached to various objects cause various problems in terms of hygiene and health. For example, conventionally, it is general that, as for inflammation caused by bacteria occurring between a dental implant and the gums, it is confirmed visually that inflammation had occurred and then the inflammation is addressed. In contrast, by using the detection apparatus according to the present invention, it is possible to perform measurement easily and quickly, and it is possible to detect before the occurrence of visible inflammation, more specifically, to detect, on the basis of a current, a situation in which the activity of bacteria increases.

In addition, for example, since bacteria attached to the endoscope can cause an infection or the like, it is particularly important to detect an abnormality related to the bacteria attached to the endoscope. With the detection apparatus according to the present invention, it is possible to reliably detect an abnormality related to bacteria with an configuration for easy and quick measuring a current between electrodes.

REFERENCE SIGNS LIST

10 Detection apparatus
11 Electrode formation unit
12 Detection Unit
13 Measurement unit
14 Adjustment unit
15 Comparison unit
16 Abnormality detection unit
17 Electron source emission unit
17a Nozzle
17b Pump
17c Electron source storage unit
18 Control unit
18a Central processing unit
18b Storage device
19a Display device
19b Input device
30 Artificial tooth
31 Electrolytic solution
32 Gums
33 Jawbone
34 Electrode
41 Electron source
42 Biofilm
50 Endoscope
51 Insertion unit
52 Operation unit

The invention claimed is:

1. A detection apparatus comprising:
an electrode formation unit configured to be brought into contact with an object to form an electrode;
a detection unit that constitutes an electrode pair with the electrode;
a measurement unit that measures a current flowing between the electrode and the detection unit; and
a determination unit that determines a presence or absence of an abnormality related to bacteria attached to the object according to the current measured by the measurement unit.

2. The detection apparatus according to claim 1, wherein the object is a dental implant.

3. The detection apparatus according to claim 2, wherein the detection unit further includes an electron source emission unit capable of emitting an electron source,
wherein the electron source emission unit includes a nozzle for emitting the electron source, an electron source storage unit in communication with the nozzle, and a pump configured to supply the electron source to the nozzle, and
wherein the electron source is glucose or lactic acid.

4. The detection apparatus according to claim 1, wherein the detection unit further includes an electron source emission unit capable of emitting an electron source,
wherein the electron source emission unit includes a nozzle for emitting the electron source, an electron source storage unit in communication with the nozzle, and a pump configured to supply the electron source to the nozzle, and
wherein the electron source is glucose or lactic acid.

5. The detection apparatus according to claim 1, further comprising a reference electrode.

6. The detection apparatus according to claim 1, wherein the determination unit includes:
a comparison unit that compares the current with a predetermined reference; and
an abnormality detection unit that detects the abnormality on the basis of a result of the comparison, and the abnormality detection unit prompts to display attention calling information in a case where the abnormality detection unit detects the abnormality.

7. The detection apparatus according to claim 6, wherein the attention calling information is information for informing that bacteria may be proliferating.

8. A data collection method comprising:
forming an electrode by bringing an electrical conductor into contact with an object in contact with an electrolytic solution;
forming an electrode pair by bringing an electrode different from the formed electrode into contact with the electrolytic solution, the electrode pair being arranged apart from each other via the electrolytic solution; and
measuring a current flowing between the electrode pair.

* * * * *